(12) United States Patent
Wilhelm et al.

(10) Patent No.: US 9,696,273 B2
(45) Date of Patent: Jul. 4, 2017

(54) REFERENCE HALF-CELL AND ELECTROCHEMICAL SENSOR WITH THE REFERENCE HALF-CELL

(71) Applicant: Endress + Hauser Conducta Gesellschaft für Mess-und Regeltechnik mbH + Co. KG, Gerlingen (DE)

(72) Inventors: Thomas Wilhelm, Halle (DE); Thomas Schroter, Jena (DE); Michael Hanko, Dresden (DE); Wolfram Nowak, Schluchtern (DE); Thilo Trapp, Aliso Viejo, CA (US)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 513 days.

(21) Appl. No.: 13/719,363

(22) Filed: Dec. 19, 2012

(65) Prior Publication Data

US 2013/0161191 A1    Jun. 27, 2013

(30) Foreign Application Priority Data

Dec. 22, 2011    (DE) .......................... 10 2011 089 671

(51) Int. Cl.
*G01N 27/30*    (2006.01)
*G01N 27/31*    (2006.01)
(Continued)

(52) U.S. Cl.
CPC ........... *G01N 27/31* (2013.01); *G01N 27/301* (2013.01); *G01N 27/333* (2013.01);
(Continued)

(58) Field of Classification Search
CPC ...... G01N 27/31; G01N 27/32; G01N 27/301; G01N 27/302; G01N 27/36; G01N 27/333;
(Continued)

(56) References Cited

U.S. PATENT DOCUMENTS 4,165,271 A * 8/1979 Kadija ................... C25B 13/04
                                                            204/252
4,218,299 A    8/1980 Lindell
(Continued)

FOREIGN PATENT DOCUMENTS

CN           1721847 A      1/2006
CN        102265147 A     11/2011
(Continued)

OTHER PUBLICATIONS

German Search Report issued in corresponding Application No. 10 2011 089 671.6, dated Sep. 13, 2012.

*Primary Examiner* — Gurpreet Kaur
(74) *Attorney, Agent, or Firm* — Mark A. Logan; PatServe

(57) ABSTRACT

A reference half-cell for application in an electrochemical sensor, comprising a housing, in which a chamber containing a reference electrolyte is formed, wherein the reference electrolyte (5, 105) is in contact with a medium surrounding the housing via a liquid junction arranged in a wall of the housing, wherein the liquid junction comprises a porous diaphragm, especially a porous ceramic diaphragm, and wherein the diaphragm has, at least partially, a coating, which comprises at least one metal.

8 Claims, 4 Drawing Sheets

(51) Int. Cl.
 *G01N 27/333* (2006.01)
 *G01N 27/401* (2006.01)
 *G01N 27/414* (2006.01)
 *G01N 27/416* (2006.01)

(52) U.S. Cl.
 CPC ......... *G01N 27/401* (2013.01); *G01N 27/414* (2013.01); *G01N 27/416* (2013.01); *Y10T 29/417* (2015.01)

(58) Field of Classification Search
 CPC ............... G01N 27/401; G01N 27/414; G01N 27/4148; G01N 27/4035; G01N 27/403
 See application file for complete search history.

(56) References Cited

U.S. PATENT DOCUMENTS

| | | | |
|---|---|---|---|
| 4,632,746 A | | 12/1986 | Bergman |
| 4,699,806 A | * | 10/1987 | Fait et al. .................. 427/126.1 |
| 5,271,820 A | * | 12/1993 | Kinlen et al. ................ 204/418 |
| 5,612,089 A | | 3/1997 | Dilmore, Jr. et al. |
| 5,683,749 A | * | 11/1997 | DuBois .................. C25B 13/04 427/243 |
| 2003/0178306 A1 | * | 9/2003 | Balisky et al. ............... 204/435 |
| 2006/0001431 A1 | * | 1/2006 | Adami et al. ................. 324/446 |
| 2006/0006075 A1 | * | 1/2006 | O'Neill ...................... 205/787.5 |
| 2006/0027453 A1 | * | 2/2006 | Catalano et al. ............. 204/435 |
| 2007/0045105 A1 | * | 3/2007 | Schussler .................. C25B 1/46 204/230.2 |
| 2008/0289956 A1 | * | 11/2008 | Schussler ...................... 204/296 |
| 2009/0263586 A1 | | 10/2009 | Goedicke |

FOREIGN PATENT DOCUMENTS

| | | |
|---|---|---|
| DE | 35 42 559 A1 | 6/1986 |
| DE | 36 36 518 A1 | 6/1987 |
| DE | 100 53 979 A1 | 5/2002 |
| DE | 696 17 437 T2 | 8/2002 |
| DE | 103 54 100 A1 | 6/2005 |
| DE | 10 2007 049 013 A1 | 4/2009 |
| EP | 1 643 242 A1 | 4/2006 |
| WO | 2011078252 A1 | 6/2011 |

* cited by examiner

REFERENCE HALF-CELL AND ELECTROCHEMICAL SENSOR WITH THE REFERENCE HALF-CELL

TECHNICAL FIELD

The invention relates to a reference half-cell and to an electrochemical sensor having such a reference half-cell.

BACKGROUND DISCUSSION

Electrochemical sensors are often used for determining concentrations of certain substances in a measured medium, both in laboratory measurements technology as well as also in process measurements technology, in many fields of chemistry, environmental analysis, biochemistry, biotechnology, pharmacy, food technology and water management. Electrochemical sensors of the field of the invention can be, for example, potentiometric or amperometric sensors. Potentiometric sensors comprise, as a rule, a measuring half-cell, which, in contact with the measured medium, forms a potential dependent on the concentration of the analyte in the measured medium, a reference half-cell, which, in contact with the measured medium, outputs a potential independent of the analyte concentration to be determined, as well as a measuring circuit, which produces a measurement signal representing the potential difference between the measuring half-cell and the reference half-cell and, in given cases, outputs such to a superordinated unit connected with the sensor, for example, a superordinated unit in the form of a measurement transmitter.

The measuring half-cell can, depending on the type of potentiometric sensor, comprise, as sensorially active component, for example, a redox electrode, an analyte sensitive coating or an ion-selective membrane. Forming a special case of ion selective membranes are pH-sensitive, glass membranes, which serve as the sensorially active component of potentiometric pH-sensors.

The reference half-cell of a potentiometric sensor is frequently embodied as an electrode of second type, for example, as a silver/silver chloride electrode (Ag/AgCl electrode). Such a reference half-cell has a reference electrolyte accommodated in a housing of an electrically insulating material, into which a chloridized silver wire extends. The reference electrolyte is, for example, a 3 molar KCl solution. Arranged in the housing wall is a liquid junction, for example, a passageway, a window of ground glass or a porous diaphragm, through which the reference electrolyte is in ionically conducting contact via a liquid-liquid interface with a surrounding medium, for example, the measured medium.

Amperometric sensors can comprise, for example, a three electrode circuit, including a working electrode, a counter electrode and a non-current carrying, reference electrode. The reference electrode, through which electrical current does not flow, referred to here and in the following likewise as a half-cell, can be embodied in equal manner as a reference half-cell of a potentiometric sensor, as an electrode of second type.

The liquid junction of a reference half-cell of the field of the invention is frequently implemented by a porous diaphragm of a ceramic material, glass or Teflon, which is introduced into the housing wall of the reference half-cell, for example, by being welded in or held in place by adhesive. The ceramic material is, above all, a zirconium dioxide ceramic. The porous structure, e.g. the number and size distribution of the pores, influences properties, such as the electrolyte outflow or the impedance of the liquid junction, decisively. Moreover, especially in the case of measuring in media with lesser conductivity, diffusion- and streaming potentials lead to measurement uncertainties.

In the article by Wolfgang Knappek entitled "Neue pH-Messketten für Labor und Prozess (New pH-measuring chains for laboratory and process)", GIT Labor-Fachzeitschrift (Laboratory Journal), September/2001, Pgs. 2-4, pH combination electrodes are described, whose reference half-cell has a platinum diaphragm as liquid junction. A platinum diaphragm is composed of a plurality of platinum wires twisted together, between which are formed hollow spaces serving as ducts, which connect the electrolyte filled, housing interior of the reference half-cell with the measured medium. The reference electrolyte flows through the ducts with uniform velocity. In this way, the diaphragm is rinsed clean at the contact with the measured solution. As a result of these characteristics, a potentiometric pH sensor having such a reference half-cell is said to possess a very short settling time to steady measured values, a high accuracy of measurement and insensitivity to influences of stirring and flowing liquid.

Disadvantageous in the case of platinum diaphragms as liquid junctions for electrochemical sensors is, however, on the one hand, the relatively high manufacturing costs and the, in comparison to conventional ceramic-, glass or Teflon diaphragms, clearly higher loss of reference electrolyte through the diaphragm during operation. This is especially disadvantageous in process applications, in which a measuring chain should work stably over longer periods of time.

SUMMARY OF THE INVENTION

It is, consequently, an object of the invention to provide a reference half-cell, which avoids, or at least lessens, the disadvantages of the state of the art.

The object is achieved by a reference half-cell for application in an electrochemical sensor including a housing, in which a chamber containing a reference electrolyte is formed, wherein the reference electrolyte is in contact with a medium surrounding the housing via a liquid junction arranged in a wall of the housing, wherein the liquid junction comprises a porous diaphragm, for example, a porous ceramic-, synthetic material (e.g. plastic)- or glass diaphragm, and wherein the diaphragm has, at least partially, a coating, which comprises at least one metal.

It has been found that such a coating not only lessens electrolyte outflow, since it effects a narrowing of the pores of the diaphragm, but also, it reduces the influence of diffusion in, and streaming potentials at, the diaphragm on the accuracy of measurement in measured media of lesser conductivity.

Such a coating comprising at least one metal is relatively easily and price favorably manufactured, so that the high manufacturing costs of a platinum diaphragm, as such is known from the state of the art, are avoided.

A metal-comprising coating is, for example, a coating, which comprises at least one metal layer, or which comprises a plurality of metal particles, especially metal clusters or larger metal grains. The coating can have one or more layers, which comprise one and the same metal, or the layers can be of different metals.

The coating does not have to cover the surface of the diaphragm completely. It should, however, cover at least a part of the surface, including at least a part of the pore inner walls.

The reference half-cell can comprise an electrode of second type contained in the chamber and acting as potential forming system, especially a silver/silver halide electrode. This can be formed by a chlorided silver wire, which extends as potential sensing element into the reference electrolyte. The reference electrolyte can be, for example, a 3 molar alkali metal halide solution, especially a 3 molar KCl solution.

The at least one metal can be selected from the group consisting of copper, ruthenium, rhodium, palladium, silver, osmium, iridium, platinum and gold. Preferably, the coating has at least one layer of at least one of these metals, whose degree of covering of the surface of the diaphragm and whose coating thickness are so dimensioned that the layer has metallic properties.

In a special embodiment, the coating has a biocidal effect. A biocidal effect is present when the coating or a substance contained in the coating is suitable, in chemical, physical or biological ways, to destroy, to discourage, to make unharmful, to avoid damage from or to combat harmful organisms in some other manner. A biocidal effect can also be achieved when the coating makes difficult, or suppresses, protein adsorption. A material for a coating with biocidal effect is, for example, silver. The biocidal effect of silver is known. It can be utilized in the case of the here described, reference half-cell to suppress biofouling, i.e. the growing of a layer of biomass, especially fungi, algae or bacteria, on the diaphragm. This biofouling can lead to drift of the reference potential and therewith to measurement errors and also lessen the response of the sensor. These phenomena can be prevented by means of a diaphragm coating, which has a biocidal effect.

The coating can have a first layer formed of at least a first metal and at least one other, second layer lying over the first layer, especially applied directly on the first layer, and composed of the first metal and/or a second metal different from the first metal.

The first and the at least one other layer can, in a first embodiment, be of one and the same metal. The applying of two layers, one lying on top of the other, effects, in such case, an increasing of the degree of covering and an increasing of the thickness of the coating, so that the pore narrowing effect and/or the metal properties of the coating are improved. Especially, the electrical conductivity of the coating can be increased in this way.

In a second embodiment, the first and the second layers can be of different metals. Through a targeted selection of a material combination of a plurality of the coating forming, individual layers, which, in given cases, are formed of different metals, a certain pore size can, with targeting, be set or a combination of a desired pore size and a desired maximal diaphragm resistance can, with targeting, be provided.

The coating can, supplementally or alternatively, comprise a first adherence promoting layer applied directly on the surface of the diaphragm. The adherence promoting layer can serve to improve the adhesion of the additional layers on the diaphragm material, which can be e.g. a ceramic material, a synthetic material (e.g. plastic) or glass. The adherence promoting layer can likewise comprise a metal, which, however, differs from the one or more metals in the one or more additional layers applied over the adherence promoting layer. In an embodiment advantageous especially for glass- or ceramic diaphragms, the adherence promoting layer can be formed by a layer comprising molecules with functional thiol groups, for example, by a thiol functionalized, silane layer. The functional thiol groups attach to a metal layer deposited over this adherence promoting layer, so that an improved adhesion and a greater durability of the metal coating are assured. The bonding action of the thiol groups is especially effective in the case of a silver-, gold- or platinum layer deposited thereon.

An electrochemical sensor of the invention for measuring at least one measured variable of a measured medium includes at least one reference half-cell according to one of the above described embodiments.

Along with that, the electrochemical sensor can comprise at least one sensorially active component in contact with the measured medium during measuring and having a property changing as a function of the measured variable to be determined, and a measuring circuit interacting with the reference half-cell and with the sensorially active component and embodied to produce a measurement signal dependent on the property of the sensorially active component and representing the measured variable.

A sensorially active component is a component of the electrochemical sensor having a property changing as a function of the measured variable to be determined, wherein the change of the property affects the measured value representing the measured variable as provided by the sensor.

The sensorially active component can comprise, for example, a metal redox electrode, a non-metallic redox electrode, the surface of a metal-metal oxide electrode, an EIS structure (EIS stands for electrolyte/insulator/semiconductor), especially an ion-selective, field effect transistor, or an ion-selective membrane, especially a glass membrane. In these embodiments, the sensor can thus be a potentiometric redox sensor, a potentiometric ion selective sensor, for example, a pH-glass electrode or other ion-selective electrode, or also a pH-ISFET sensor.

In an alternative embodiment, the electrochemical sensor can have, besides the reference half-cell, supplementally a working electrode and a counter electrode, which, with the reference half-cell, form a three electrode arrangement, and connected with the three electrode arrangement, a control circuit, especially a potentiostatic or galvanostatic, control circuit, which is embodied to set a predetermined desired voltage between the counter electrode and the reference electrode, and to register, in such case, the electrical current flowing through the measured medium between the counter electrode and the working electrode, especially for performing amperometric or potentiometric measurements.

The invention relates also to a method for manufacturing a reference half-cell according to one of the above described embodiments. In this method, a porous diaphragm, e.g. a ceramic diaphragm, a plastic diaphragm, especially a Teflon diaphragm, or a porous glass diaphragm, is provided in a housing wall of a housing forming a chamber for accommodating a reference electrolyte of the reference half-cell, wherein the diaphragm, especially before or after the connecting of the diaphragm with the housing wall, is coated with a coating comprising at least one metal. The connection between the diaphragm and the housing wall can occur by material bonding, for example, by adhesive or by welding, e.g. creating the bond by glass melting.

The coating of the diaphragm with the coating comprising at least one metal can comprise steps as follows:
  providing a porous stock;
  contacting the stock with a solution containing the at least one metal in the form of a metal salt or in the form of particles, especially colloidal particles;
  depositing from the solution a metal-comprising coating of the porous stock; and isolating a segment of the coated porous stock for forming the diaphragm.

The porous stock, can be, for example, a porous ceramic stock, a porous plastic stock, e.g. a porous Teflon stock, or a glass stock having a plurality of pores. It can be advantageously rod-shaped, so that the segments can be formed by sawing off or breaking off sections of the rod-shaped stock.

Optionally, the stock can, before the contacting with the solution containing the metal, be cleaned and/or the surface of the stock activated by a chemical treatment.

In this method variant, a larger porous stock can be coated. For this, the stock can be immersed into the solution containing the metal and the liquid sucked through the pores of the stock, before the metal is deposited on the surface of the stock, especially also in the pores—for example, by means of a thermal treatment, by a currentless deposition or by means of a galvanic deposition method. The coated stock can then be divided into a number of segments (for example, by sawing apart or by breaking), each of which is then placed as diaphragm in a housing wall of a reference electrode and connected therewith by material bonding.

In another method variant, the coating of the diaphragm with the coating comprising at least one metal can comprise steps as follows:
  contacting the diaphragm connected with the housing wall by material bonding with a solution containing the at least one metal in the form of a metal salt or in the form of particles, especially colloidal particles; and
  depositing a metal-comprising coating of the diaphragm from the solution.

Optionally, the diaphragm can, before the contacting with the solution containing the metal, be cleaned and/or the surface of the diaphragm activated by a chemical treatment.

In this method variant, the housing with the diaphragm connected therewith can be immersed into the solution containing the metal. By supplying the chamber formed in the housing and connected with the diaphragm with negative pressure, the liquid can be drawn into the pores of the diaphragm, so that is assured that the coating forms also within the pores. The deposition of the metal coating can occur in equal manner to that described in the previous method variant.

The depositing of a metal-comprising coating from the solution containing the metal in the form of a metal salt can be performed in both variants, for example, currentlessly or galvanically.

The depositing of a metal-comprising coating from the solution containing the metal in the form of a metal salt or in the form of nano particles, especially colloidal particles, can be performed by thermal treatment, especially firing, of the porous stock, or diaphragm, supplied with the solution. Such solutions are known, for example, for metallizing porcelain. For example, firing lacquers are commercially obtainable for applying a gold- or platinum edge on porcelain.

Before depositing the coating comprising at least one metal, a layer promoting adhesion of the metal-comprising coating can be applied on the stock, or on the diaphragm.

BRIEF DESCRIPTION OF THE DRAWINGS

The invention will now be described in greater detail based on the examples of embodiments illustrated in the drawing, the figures of which show as follows.

DETAILED DISCUSSION IN CONJUNCTION WITH THE DRAWINGS

Figure 1:
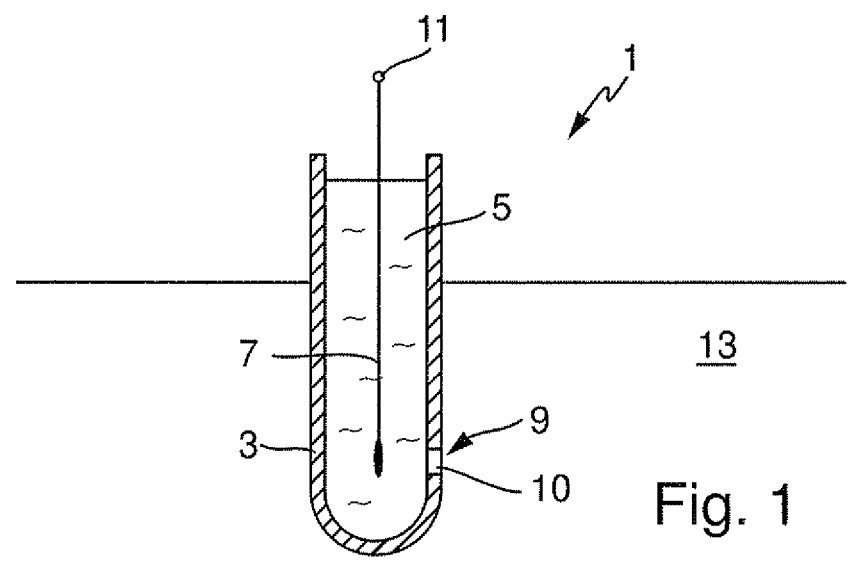
FIG. 1 is a schematic representation of a reference half-cell with a diaphragm, which has a coating comprising at least one metal.

FIG. 1 shows a schematic representation of a reference half-cell 1 with a rod-shaped, essentially cylindrical housing 3, in which a chamber is formed filled with a reference electrolyte 5. The housing 3 can be formed of an electrically insulating material, for example, glass or a synthetic material, such as a plastic. Reference electrolyte 5 is, for example, an aqueous 3 molar KCl solution or some other alkali metal halide solution. Reference electrolyte 5 is, via a liquid junction 9 formed by a porous diaphragm 10 arranged in the wall of the housing 3, in conically conducting contact with a measured medium 13 in which the reference half-cell 1 is at least sectionally immersed for performing electrochemical measurements, for example, potentiometric or amperometric measurements. Diaphragm 10 can be formed, for example, of a ceramic material, a porous glass material or a porous synthetic material, e.g. the plastic, Teflon. Extending into the reference electrolyte 5 is a potential sensing element 7 in the form, for example, of a chlorided silver wire. The potential sensing element 7 forms, with the reference electrolyte 5 in contact via the liquid junction 9 with the measured medium 13, a reference electrode of second type, in the present example an Ag/AgCl, reference electrode, which outputs via the connection 11 of the potential sensing element 7 a stable potential independent of the pH value or other ion concentrations of the measured medium.

Diaphragm 10 includes, for lessening the stirring-, or liquid flow, dependence of the reference half-cell potential tappable at the connection 11 and for lessening of the outflow of reference electrolyte from the housing 3 into the measured medium 13, a coating, which comprises at least one metal. The coating can be a purely metal coating of one or more metal layers with metallic properties. If the coating is a plurality of individual layers, different individual layers can be of different metals. Advantageously, the coating has especially a certain electrical conductivity.

The coating effects, as already described above, a narrowing of the pores of the diaphragm and, so, lessens the flow of reference electrolyte out through the diaphragm 10. As can be shown based on measurements further discussed below, the diaphragm resistance is not significantly increased, in spite of the pore narrowing. If suitable biocidally acting metals are used for the coating, such as, for example, silver or copper, the coating can simultaneously serve to prevent growth of microorganisms in and on the diaphragm 10 and thereby avoid related disturbances of the reference half-cell, for example, a drifting of the potential or even a complete failure of the reference half-cell 1.

Metals suitable for the coating include, for example, silver, gold, platinum, copper, iridium, osmium, palladium, rhodium and ruthenium. Metals with biocidal effect include, for example, silver or copper.

Figure 2:
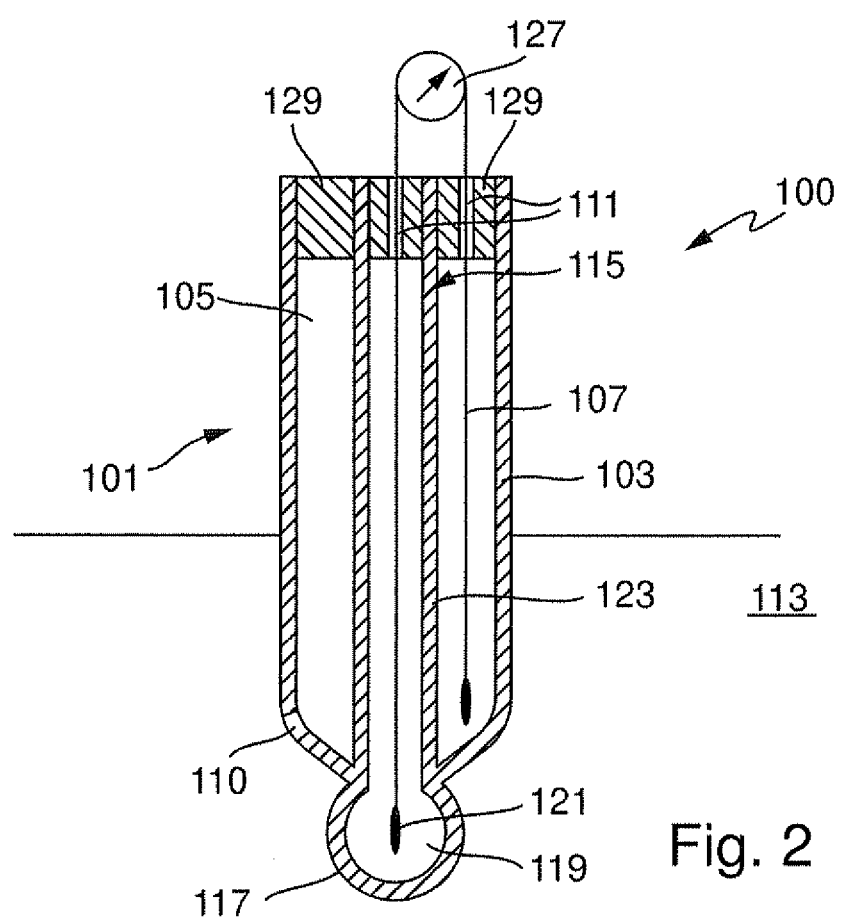
FIG. 2 is a schematic representation of a pH measuring chain in the form of a combination electrode with a reference half-cell, whose diaphragm has a coating comprising at least one metal.

FIG. 2 shows, schematically, a potentiometric pH combination electrode 100 as an example of an electrochemical sensor with a reference half-cell. Combination electrode 100 includes a reference half-cell 101 and a measuring half-cell 115, which are formed in a shared, rod-shaped housing of an insulating material, for example, glass. The housing includes an inner tube 123, in which measuring half-cell 115 is formed. The inner tube 123 is closed on its front end by a pH-sensitive, glass membrane 117, on which forms, in contact with the measured medium 113, a potential dependent on the pH value of the measured medium 113. Contained in the inner tube 123 is an inner electrolyte 119, for example, a pH buffer solution, into which a potential sensing element 121 extends. The potential sensing element 121 can be formed, for example, of a chlorided silver wire.

The reference half-cell 101 is arranged in an annular chamber, which is formed between the inner tube 123 and an outer tube 103 surrounding the inner tube 123. Outer tube 103 is connected at its front end in the region of the membrane 117 with the inner tube 123. Contained in the annular chamber is a reference electrolyte 105, for example, a 3 molar KCl solution, into which extends a potential sensing element 107 formed by a chlorided silver wire. Arranged in the outer tube 103 as liquid junction between the reference electrolytes 105 and a measured medium 113, into which the combination electrode 100 extends in measurement operation, is a diaphragm 110, which has a coating, especially a metallic coating, comprising at least one metal. The coating can be embodied in the same manner as the coating of the diaphragm 10 described in connection with the reference half-cell 1 of FIG. 1.

On its back end facing away from the measured medium 113, the combination electrode 100 is provided with a suitable plug 129, which seals the inner tube 123 and the annular chamber formed between inner tube 123 and outer tube 103 to liquid. The potential sensing elements 121, 107 of the measuring- and reference half-cells are led through the plug 129 by means of cable guides 111, 125. Potential sensing elements 121, 107 are connected with a measuring circuit 127, which registers the potential difference tappable on the potential sensing elements 107, 121 and representing the pH value of the measured medium 113. In given cases, measuring circuit 127 transforms and/or amplifies the potential difference to be output as measurement signal of the combination electrode 100. In such case, the measuring half-cell 115 represents a first galvanic half element, which is in contact with the measured medium 113 via the pH-sensitive glass membrane 117, while the reference half-cell 101 forms a second galvanic half element. The potential difference registerable between the potential sensing elements 107, 121 corresponds thus to the galvanic cell voltage of the combination electrode 100. The galvanic cell voltage depends on the pH value of the measured medium 113.

Measuring circuit 127 can be embodied as an electrical or electronic circuit arranged in a plug head (not shown) of the combination electrode 100. In such case, the plug head of the combination electrode 100 can be connected by means of a cable connection, or wirelessly, for communication with a superordinated unit, for example, a measurement transmitter, a computer or a process control station. Measuring circuit 127 is correspondingly embodied to output the measurement signal to the superordinated unit, which processes the measurement signal, outputs such via a user interface, stores and/or forwards such to another superordinated unit, e.g. a process control station.

Different method variants for forming an at least one metal-comprising, especially metallic, coating of a diaphragm will now be described. Such variants are suitable, for instance, for manufacturing a diaphragm for a reference half-cell of FIG. 1 or for a reference half-cell embodied as a component of a combination electrode of FIG. 2. As explained above, a reference half-cell of the form shown in FIG. 1 can be applied advantageously in a large number of different electrochemical sensors, especially in potentiometric sensors or in amperometric sensors.

Common to all of the here described method variants is that a porous substrate, for example, a diaphragm already held in a housing wall of a reference half-cell blank, or a porous stock, from which later a diaphragm is to be manufactured, is supplied with a solution, from which a metal-comprising coating, especially a metallic coating, will be deposited on the surface of the diaphragm. The terminology, "surface of the diaphragm" refers here to the surface of the porous structure, thus also to the inner walls of the pores of the diaphragm.

In a first method variant, an uncoated diaphragm can be provided, which is already connected by material bonding with a housing wall of a tubular blank, from which later a reference half-cell of FIG. 1 or a reference half-cell of a combination electrode of FIG. 2 will be produced. In order to supply the diaphragm with the solution, from which a metal coating will be deposited on the surface of the diaphragm, the blank can be so immersed into the solution, that the diaphragm is wetted thereby. In order to assure that the solution also penetrates into the pores of the diaphragm, so that the coating also is formed at least on the pore walls of the larger pores, the solution can be drawn through the pores of the diaphragm into the housing interior of the blank by producing a negative pressure in the tubular housing of the blank.

With this method variant, an option is to provide not only the diaphragm, but, instead, also the entire liquid immersed, outer surface of the reference half-cell housing with a metal coating. This can be desired, when a biocidal effect of the coating is important for the planned application of the reference half-cell. If the biocidal coating covers a surface region of the reference half-cell beyond that of the diaphragm, then biofouling, i.e. the growth of an undesired biofilm on the outer surface of the reference half-cell, can be more effectively suppressed.

In another method variant, for example, cylindrical, porous stock is supplied with the liquid, especially immersed into such, and the metal coating deposited from this solution onto the surface of the stock. The coated stock can then be divided into individual segments, each of which can then be welded as diaphragm into its own rod-shaped housing blank to form a reference half-cell of FIG. 1 or FIG. 2. This method variant is suited preferably for batch production of reference half-cells, in the case of which a coating of only the diaphragm is desired. Especially, in this method, by means of a single coating step, a plurality of coated diaphragms can be produced, which then can be mounted in a corresponding number of reference half-cell blanks by welding or adhesion.

Also in this method variant, it is advantageous to draw the liquid containing the metal to be deposited into the pores of the stock by applying a negative pressure, in order to assure that the metal is deposited also within the pores. Alternatively, a better wetting of the pore interiors can be achieved in the case of both method variants also by means of an ultrasonic bath.

Suited as material for a ceramic substrate for manufacturing a reference half-cell with a coated ceramic diaphragm, independently of whether it is coated in the form of ceramic stock or in the form of a ceramic diaphragm already bonded in a wall of a reference half-cell blank, is, for example, CaO-stabilized $ZrO_2$ with a pore diameter of 450 nm. Another suitable material is $Y_2O_3$-stabilized $ZrO_2$ with a pore diameter of 1.8 μm.

Before applying the coating, the surface of the diaphragm, or of the stock, can be thoroughly cleaned with a cleaning liquid, for example, with an organic solvent, such as acetone. In an optional, additional step, the surface can, after removal of the cleaning liquid, be cleaned and/or activated with "piranha" solution for the subsequent coating. Piranha solution is produced by mixing 98% sulfuric acid with 30% hydrogen peroxide solution in a volume ratio between 1:1 and 3:1. The piranha solution is subsequently removed by thorough re-rinsing with water. Then, a renewed cleaning step can occur, in which the diaphragm, or the porous stock, is rinsed with ethanol, in order to remove residual water possibly still in the pores. Following a terminal, drying step, the diaphragm, or the stock, is supplied with the coating solution.

A first option for depositing a metal-comprising coating is to supply the diaphragm with a metal salt solution and then to deposit, by a thermal and/or chemical treatment, the metal in the form of a layer on the diaphragm surface. For this, suited as metal salt solution for producing a platinum layer is, for example, hexachloroplatinic acid. This treatment can, in given cases, be repeated multiple times, in order to achieve a sufficient surface coating, or a sufficient coating thickness.

A second opportunity for depositing a metal coating is a galvanic deposition, in the case of which the cathode is in contact with a side of the porous substrate to be coated and is immersed in a metal salt solution accommodated in a container. The anode can advantageously be present in the container, for example, secured in or on a container wall. For galvanically producing a silver metal layer, the metal salt solution can be, for example, a silver nitrate solution and the anode can be a silver anode. Between the cathode and the anode is applied a voltage required for galvanic deposition of silver on the cathode. The silver deposited on the cathode grows from the contact between cathode and substrate through the pores of the diaphragm and forms, thus, a coating of the porous substrate within and outside of the pores.

A third option for depositing a metal coating on the substrate is an electrically currentless deposition, for example, for producing a platinum layer by means of a solution comprising hexachloroplatinic acid and ascorbic acid. In given cases, the substrate can be supplied multiple times, in sequence, with the solution, in order to assure a sufficient thickness of the coating.

A fourth option for depositing a metal coating on the substrate comprises applying a firing lacquer and subsequent firing of the lacquer for producing a metal layer. Such firing lacquers are commercially obtainable and are conventionally used to produce metal coatings on porcelain, e.g. for decoration of porcelain dishware. In order to assure that the coating also forms within the pores in the case of this method, the firing lacquer can be sucked through the porous structure. Firing leads to a metallic, conductive coating. In given cases, the applying and firing of the lacquer can be repeated multiple times.

Options include also combinations of these methods, in order, for example, to produce a coating of a plurality of individual layers, especially also of a plurality of individual layers, which comprise different metals. In this way, it is possible, with targeting, to establish a certain pore size or to provide a combination of a desired pore size and a desired maximal diaphragm resistance.

A biocidally acting coating can, moreover, be produced according to the following method: The cleaned and dried substrate, for example, a porous ceramic substrate, especially a $ZrO_2$-ceramic, is supplied in a first step with a 2% solution of (3-mercaptopropyl)trimethoxy silane. In order to supply the surface of the substrate as completely as possible with the solution, also within the pores, the solution can, for example, be drawn through the substrate by suction. Thereafter, a rinse step with toluene can be performed. Then, the substrate is dried. The, substrate, silanized in this way, is, thereafter, stored for a certain time, preferably at least 24 hours, in order to achieve a degree of cross linking of the silane on the surface. Then, the substrate is, first of all, immersed in a 2% silver nitrate, dimethyl sulfoxide solution ($AgNO_3$/DMSO solution) and the solution drawn through the substrate by suction, in order to achieve an as complete as possible supplying of the substrate surface, including the pores, with the solution. Immediately, then, the substrate is immersed in a 0.1 molar lithium borohydride, dimethyl sulfoxide solution ($LiBH_4$/DMSO solution) and the solution drawn through the substrate by suction. The lithium borohydride reduces silver ions on or in the silane layer to elemental silver, which bonds with the thiol-functionalities of the silane layer. The bonding of the silver coating via the thiol groups of the silane layer to the thereunder lying substrate improves adhesion of the silver coating significantly compared with a direct bonding of the silver coating to the substrate surface. In this way, a significantly longer storability of the silver coating can be assured in comparison with a silver coating applied directly on the substrate, also in the case of difficult environmental conditions in measurement operation with the modified reference half-cell. For achieving a desired layer thickness on the substrate, it can, when required, be supplied multiple times alternately with the $AgNO_3$/DMSO solution and the $LiBH_4$/DMSO solution.

A series of experimental investigations with reference half-cells, respectively, electrochemical sensors, having a ceramic diaphragm coated with at least one metal will now be described in greater detail. The invention is, however, equally applicable for reference half-cells and sensors with porous diaphragms of other materials, especially for reference half-cells and sensors with synthetic material- or glass diaphragms.

Tests showed that *Saccharomyces cerevisiae* applied as test organism did not grow on ceramic diaphragms modified with a silver coating as above described. In an additional experiment, pH combination electrodes, whose diaphragms had a silver coating produced according to the above described method and bonded to the ceramic surface via a silane layer with thiol functionalities, were subjected to long term service in a fermenter. For this, the combination electrodes were applied in a fermenter, which contained the green algae, tetraspora lubrica, as test organism. It is a known property of this algae that it grows vigorously on surfaces.

Figure 3:
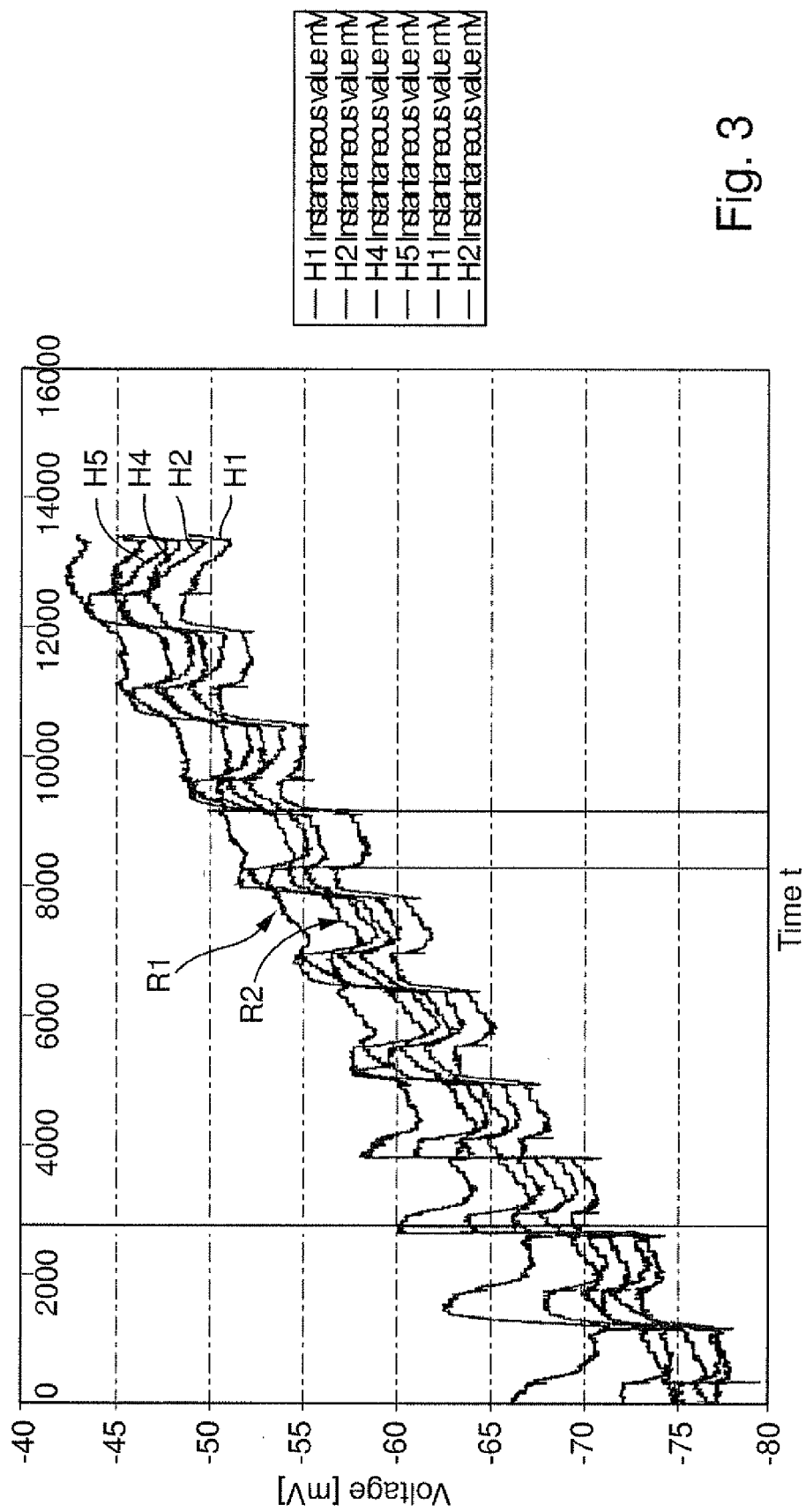
FIG. 3 is a graph, in which is presented for proof of a biocidal effect of a silver coating of a ceramic diaphragm of a reference electrode, the measurement voltage curves of pH combination electrodes with diaphragms coated in such a manner and, for comparison, the measurement voltage curves of pH combination electrodes with conventional diaphragms in measurement operation in a fermenter.

The graph of FIG. 3 shows the measurement signals of four such pH combination electrodes (H1, H2, H4, H5) in fermentation operation plotted as a function of time. For comparison, moreover, the measurement signals of two comparison combination electrodes (R1, R2) with a conventional ceramic diaphragm are plotted.

The evident continuous rise of the measurement signal results from the progress of the non-regulated fermentation process, in the case of which the pH value of the measured medium becomes continuously more alkaline due to the metabolism of the green algae. The short term, greater increases superimposed on the continuously rising pH value and the, in each case, adjoining short term decline of the measurement signal results from simulation of a day/night cycle performed in the experiment. The measured medium was alternately illuminated and, thereafter, shaded. In the case of illumination, the $CO_2$ content of the measured medium is reduced by the metabolism of the green algae, which leads to a rise of the pH value, while, in the case of darkness, the $CO_2$ content goes up again, which effects a decline of the pH value of the measured medium.

It is evident from FIG. 3 that the comparison combination electrodes with the conventional ceramic diaphragms reflect the pH value curve correctly at the beginning of the measurements, but, for instance, from the fifth day/night-cycle, the short term, pH value fluctuations of the measured medium are no longer precisely registered. In contrast therewith, all the combination electrodes with modified diaphragms show, over the entire duration of the experiment, an unchanged, high accuracy of measurement. This is attributable to the fact that, on the conventional ceramic diaphragms in the course of fermentation operation, growth of the algae contained in the measured medium occurs, while, due to the biocidal effect of the silver coating on the ceramic diaphragms of the modified combination electrodes, no, or only a negligible, growth occurs.

As already mentioned, metal-comprising coating of a ceramic diaphragm in a sensor leads also to a lessening of the liquid flow- or stirring dependence of the sensor signal in media of lesser conductivity and to a reduction of out flow of reference electrolyte through the diaphragm, without significant increasing of the diaphragm resistance. In the following, some measurement results demonstrating this will now be presented.

Figure 4:
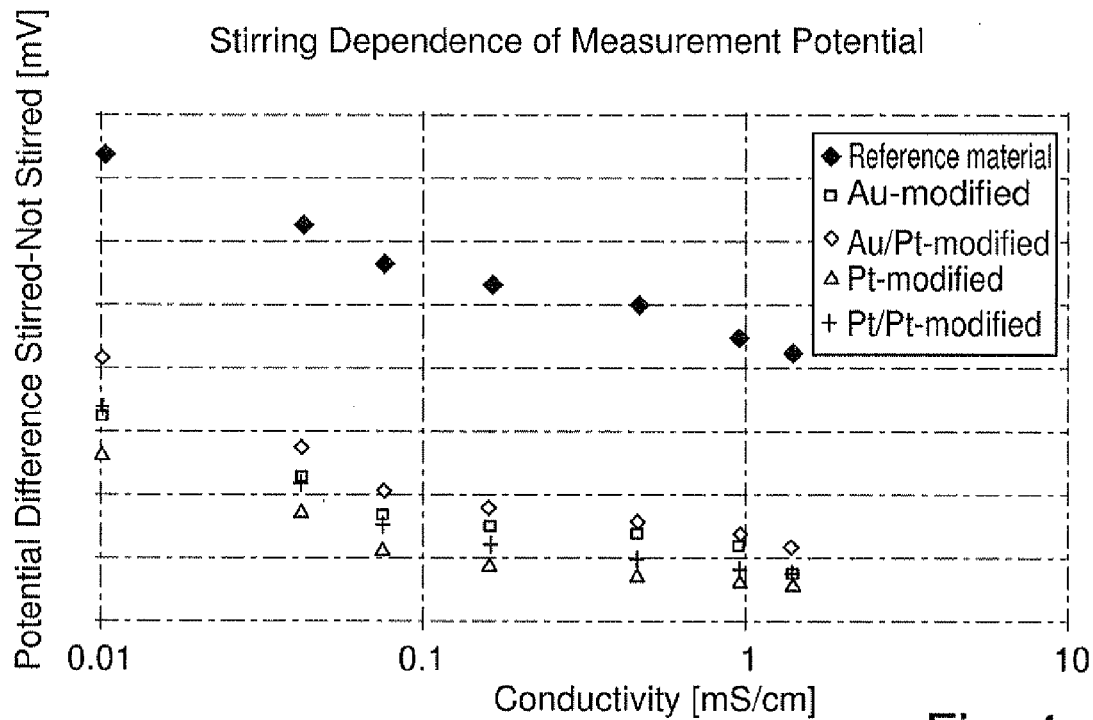
FIG. 4 is a graph for illustrating the stirring dependence of the potential output from different reference half-cells as a function of the conductivity of a measured medium.

FIG. 4 shows a graph illustrating the stirring dependence of the potential output by different test reference half-cells as a function of the conductivity of a measured medium. Used for the measurements for the graph were different test reference half-cells having a ceramic diaphragm with a metal coating. The test reference half-cells were produced by supplying various ceramic substrates of a CaO-stabilized, $ZrO_2$-ceramic with a pore diameter of 450 nm and a flow rate of 4.85 ml/d, as well as a resistance of 152 ohm/mm (material M1) with a firing lacquer containing the metal to be provided on the ceramic substrate. By subsequent firing, the metal coating was formed. From the coated ceramic substrates, segments were separated and welded into different reference half-cell housings. The reference half-cells were filled with a 3 molar KCl solution and contained a potential sensing element of chlorided silver wire. The ceramic diaphragm of a first test reference half-cell was modified in this way with a gold coating (open squares), that of an additional test reference half-cell with a platinum coating (open triangles), that of a third test reference half-cell with a first layer of gold and a thereover arranged, platinum layer (open diamonds) and the ceramic diaphragm of a fourth test reference half-cell with two platinum layers arranged on top of one another (crosses). A comparison measurement was made with a conventional reference half-cell having an uncoated ceramic diaphragm of the ceramic material also used for the test reference half-cells (filled out diamonds).

The test reference half-cells were placed in a measured medium of lesser conductivity, i.e. a conductivity of less than 10 mS/cm, and the potential tappable on the potential sensing element of the test reference half-cells measured relative to the glass half-cell both in the stirred measured medium as well as also in the resting measured medium. The difference between the potentials measured in the flowing state and those in the resting state is plotted as a function of the conductivity of the measured medium in FIG. 4. This difference is here also referred to, for short, as stirring- or liquid flow dependence of the measurement signal. As evident from FIG. 4, this stirring- or liquid flow dependence is clearly smaller in the case of the test reference half-cells than in the case of the conventional reference half-cell.

Figure 5:
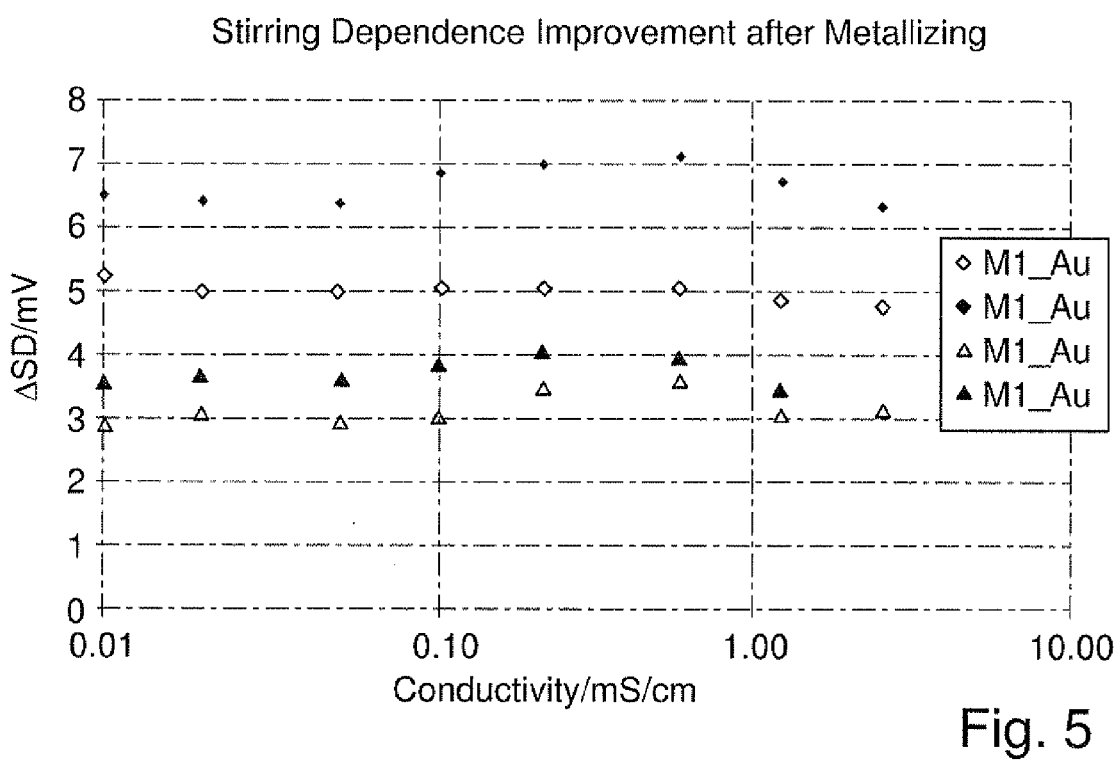
FIG. 5 is a graph, in which is presented the lessening of stirring dependence of various reference electrodes with coated ceramic diaphragm in comparison to a conventional ceramic diaphragm.

FIG. 5 shows a graph, in which the lessening of stirring dependence ($\Delta$ SD) of the test reference half-cells with coated ceramic diaphragm is presented relative to the conventional reference half-cell with uncoated ceramic diaphragm as a function of the conductivity of the measured medium. The terminology "lessening of stirring dependence" refers here to the difference between the stirring- or liquid flow dependence of the test reference half-cells and that of the conventional reference half-cell presented in FIG. 4. In FIG. 5, the open diamonds represent the results obtained with the test electrode, whose diaphragm has a gold coating. The closed diamonds give measurement points, which were obtained with the test electrode, whose diaphragm was modified with a gold layer and an overlying platinum layer. Measurement points, which were obtained with the test reference half-cell, whose diaphragm has a platinum coating are presented with open triangles. The closed triangles represent measurement results, which were obtained with the test reference half-cell, whose diaphragm has a coating of two platinum layers lying on top of one another.

Figure 6:
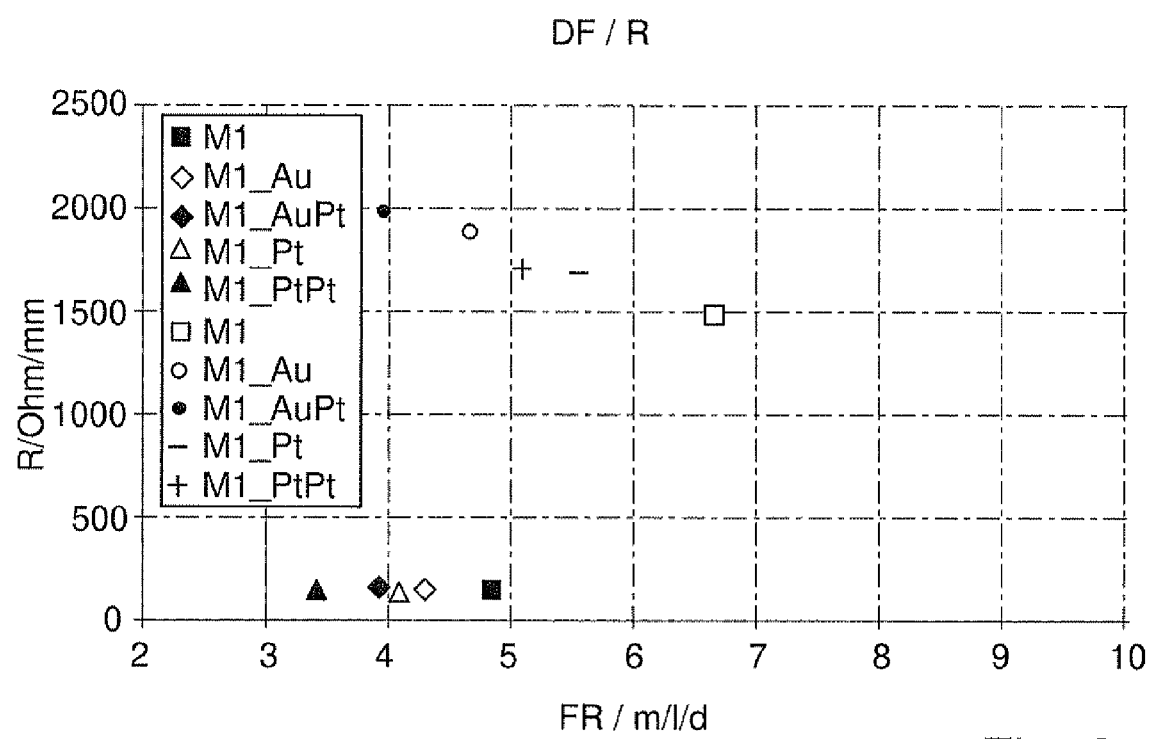
FIG. 6 is a graph, in which are presented experimentally ascertained flow and experimentally ascertained diaphragm resistance for different coated ceramic diaphragms.

FIG. 6 shows results of flow- and resistance measurements on test ceramic diaphragms with metal coating. Flow was measured by placing reference half-cell tubes filled with 3 molar KCl solution, and each having a test ceramic diaphragm arranged in its wall, in a defined volume of DI-water and supplying each tube with a defined pressure. From the gradual change over time of the conductivity of the DI-water due to the escape of KCl solution from the reference half-cell tubes with accompanying enriching of the DI-water with KCl, flow through each of the test ceramic diaphragms was ascertained.

The resistance of the test diaphragms was ascertained by measuring conductivity between a first platinum electrode arranged in the interior of the reference half-cell tube and a second platinum electrode arranged in a medium surrounding the reference half-cell tube.

The measured values illustrated in the graph of FIG. 6 were ascertained for different test ceramic diaphragms. A first group of test diaphragms was made of coated ceramic diaphragms of CaO-stabilized $ZrO_2$ (M1) with a pore diameter of 450 nm, a flow rate of 4.85 ml/d and a resistance of 152 ohm/mm (values in the uncoated state), with a gold coating (open diamond), a coating of a gold layer and a platinum layer lying thereon (filled out diamond), a coating formed of a single layer of platinum (open triangle), and a coating formed of two platinum layers lying on top of one another (filled out triangle). For comparison, moreover, flow- and resistance measurements were performed on an uncoated ceramic diaphragm of the said material (filled out square).

A second group of test diaphragms was made of coated ceramic diaphragms of $Y_2O_3$-stabilized $ZrO_2$ (M2) with a pore diameter of 1.8 μm, a flow rate of 6.7 ml/d and a resistance of 1486 ohm/mm (values in the uncoated state), with a gold coating (open circle), a coating formed of a gold layer and a platinum layer lying thereon (filled out circle), a coating formed a of a single platinum layer (minus sign) and a coating formed of two platinum layers lying on top of one another (plus sign). For comparison, moreover, flow and resistance measurements were performed on the uncoated ceramic material (open square).

FIG. 6 shows measured diaphragm resistance R plotted against flow rate in ml/d. Through the coating of the ceramic diaphragms, the flow rate of the material M1 was reduced by up to 30% and the flow rate of material M2 by up to 40%. In such case, a relatively small rise of the diaphragm resistance in the case of the diaphragms formed of the material M1 of up to 6% and in the case of the diaphragms formed of the material M2 of up to 33% was detected.

The invention claimed is:

1. A method for manufacturing a reference half-cell, wherein the reference half-cell comprises:
   a housing in which a chamber containing a reference electrolyte is formed, wherein the reference electrolyte is in contact with a medium surrounding the housing via a liquid junction disposed in a wall of the housing wherein
   the liquid junction comprises a diaphragm of porous media,
   the diaphragm having an outer surface defining a volume, the volume including a plurality of pores within the media, each of the plurality of pores having an inner surface,
   the diaphragm further including a coating distributed on the inner surfaces of the plurality of pores and on the outer surface, such that the coating at least partially covers the inner surfaces and the outer surface, wherein the coating includes at least one metal, the method comprising the steps of:
   providing a porous diaphragm in a housing wall of a housing;
   forming a chamber for accommodating a reference electrolyte in the housing of the reference half-cell; and
   coating the diaphragm with a coating comprising at least one metal,
   wherein the step of coating comprises contacting the diaphragm with a solution containing the at least one metal in the form of a metal salt or in the form of nano particles and depositing from the solution the coating within the pores and on the surface of the diaphragm.

2. The method as claimed in claim 1, wherein prior to providing the porous diaphragm in the housing wall, the method further comprises the following steps:
   providing a porous stock;
   contacting the stock with a solution containing the at least one metal in the form of a metal salt or in the form of nano particles;
   depositing from the solution the coating within the pores and on the surface of the porous stock; and
   isolating a segment of the coated porous stock for forming the diaphragm.

3. The method as claimed in claim 2, wherein
   the depositing of the coating from the solution containing the metal in the form of a metal salt is performed currentlessly or galvanically.

4. The method as claimed in claim 2, wherein
   the depositing of the coating from the solution containing the metal in the form of a metal salt or in the form of nano particles is performed by thermal treatment of the stock or diaphragm supplied with the solution.

5. The method as claimed in claim 2, wherein
   before depositing the coating comprising at least one metal, a layer promoting adhesion of the metal-comprising coating is applied on the stock.

6. The method as claimed in claim 2,
   wherein the porous stock comprises a plurality of pores and
   wherein the step of contacting the stock with the solution comprises drawing the liquid through the pores before the metal is deposited within the pores and on the surface of the stock.

7. The method as claimed in claim 1,
   wherein the step of contacting the diaphragm with a solution containing the at least one metal comprises drawing the liquid into the pores of the diaphragm and forming the coating also within the pores.

8. The method as claimed in claim 1, wherein the porous media is one of the group of zirconium dioxide, ceramic, glass, and Teflon.

* * * * *